(12) United States Patent
Kusaka et al.

(10) Patent No.: US 7,771,575 B2
(45) Date of Patent: Aug. 10, 2010

(54) ANALYTICAL TOOL

(75) Inventors: Yasuhide Kusaka, Kyoto (JP);
Yoshiharu Sato, Kyoto (JP); Yoshimitsu Morita, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 894 days.

(21) Appl. No.: 10/532,789

(22) PCT Filed: Oct. 22, 2003

(86) PCT No.: PCT/JP03/13505

§ 371 (c)(1),
(2), (4) Date: Apr. 25, 2005

(87) PCT Pub. No.: WO2004/038397

PCT Pub. Date: May 6, 2004

(65) Prior Publication Data

US 2006/0042941 A1    Mar. 2, 2006

(30) Foreign Application Priority Data

Oct. 25, 2002    (JP) .............................. 2002-311712

(51) Int. Cl.
*G01N 27/327* (2006.01)
*G01N 27/00* (2006.01)
(52) U.S. Cl. ..................... 204/403.02; 204/400; 422/55
(58) Field of Classification Search . 204/403.1–403.15; 422/55–58
See application file for complete search history.

(56) References Cited

U.S. PATENT DOCUMENTS

| 5,320,732 | A |   | 6/1994 | Nankai et al. |
| 5,582,697 | A |   | 12/1996 | Ikeda et al. |
| 5,628,890 | A | * | 5/1997 | Carter et al. ........... 204/403.05 |
| 5,985,116 | A | * | 11/1999 | Ikeda et al. ............ 204/403.04 |
| 7,267,750 | B2 | * | 9/2007 | Watanabe et al. ...... 204/403.04 |
| 2003/0098234 | A1 |   | 5/2003 | Hasegawa et al. |
| 2005/0072670 | A1 |   | 4/2005 | Hasegawa et al. ...... 204/403.01 |

FOREIGN PATENT DOCUMENTS

| JP | 8-10208 | 1/1996 |
| JP | 8-320304 | 12/1996 |
| JP | 9-43189 | 2/1997 |
| JP | 2001-201480 | 7/2001 |
| JP | 2002-181757 | 6/2002 |
| JP | 2002-202283 | 7/2002 |
| JP | 2003 254933 | 9/2003 |
| WO | WO 02/10734 | 2/2002 |
| WO | WO 02057767 A1 * | 7/2002 |

* cited by examiner

*Primary Examiner*—Alex Noguerola
(74) *Attorney, Agent, or Firm*—Hamre, Schumann, Mueller & Larson, P.C.

(57) ABSTRACT

The present invention relates to an analytical tool (1) comprising a substrate (10), a capillary (13) which is formed on the substrate (10) and into which a sample liquid is to be loaded by movement of the sample liquid in the capillary. The substrate (10) is provided with a liquid movement preventer for preventing the sample liquid loaded into the capillary (13) from moving further. Preferably, the liquid movement preventer includes a stepped portion (18B) projecting from the substrate or a recess provided at the substrate.

7 Claims, 12 Drawing Sheets

ANALYTICAL TOOL

This application is a national stage 371 of PCT/JP03/13505, filed on Oct. 22, 2003, which claims foreign priority from Japanese application 2002-311712, filed on Oct. 25, 2002.

TECHNICAL FIELD

The present invention relates to an analytical tool used for analyzing a particular component contained in a sample liquid.

BACKGROUND ART

As an easy method for measuring a glucose level in blood, a disposable biosensor is used (See JP-B2-8-10208, for example). An example of such biosensor is shown in FIGS. 11 and 12 of the present application. In the illustrated biosensor 9, a responsive current which is necessary for the computation of a blood glucose level is measured by utilizing a working electrode 90 and a counter electrode 9. The biosensor 9 includes a substrate 92, and a cover 94 stacked on the substrate via a spacer 93 formed with a slit 93a. These components 92-94 define a capillary 95 on the substrate 92. The capillary 95 is utilized for moving blood by capillary action and retaining the blood. The capillary 95 communicates with the outside through an introduction port 96 for introducing blood and an air vent 97 for discharging air from the capillary 95 when the blood moves in the capillary 95.

On the substrate 92 are provided an insulating layer 98 and a reagent portion 99. The insulating layer 98 covers the working electrode 90 and the counter electrode 91 while exposing opposite ends 90a, 90b of the working electrode 90 and opposite ends 91a, 91b of the counter electrode 91. The reagent portion 99 covers the ends 90a, 91a of the working electrode 90 and the counter electrode 91 and is in a solid state containing oxidoreductase and an electron mediator.

To measure a blood glucose level, with a biosensor 9 mounted to a concentration measuring apparatus (not shown), blood BL is introduced into the capillary 95 through the introduction port 96, as shown in FIG. 13. In the capillary 95, the movement of the blood BL stops at the edge 97a of the air vent 97, and the reagent portion 99 is dissolved by the blood BL, whereby a liquid phase reaction system is established. A voltage can be applied to the liquid phase reaction system by the power source of the concentration measuring apparatus through the working electrode 90 and the counter electrode 91. The responsive current upon the voltage application can be measured at the blood glucose level measuring apparatus (not shown) by utilizing the working electrode 90 and the counter electrode 91. The responsive current is obtained as the reflection of the amount of electrons transferred between the electron mediator and the end 90a of the working electrode 90 in the liquid phase reaction system. Thus, the responsive current relates with the amount of the electron mediator which exists around the working electrode 90 and which is capable of transferring electrons between the end 90a of the working electrode 90.

However, when the concentration measurement is performed by using the biosensor 9, the measurement result is sometimes higher than the actual concentration. To find out the cause, the inventors of the present invention measured the change of oxidation current with time by using some samples. As a result, it is found that, in some cases, as is in the time course of oxidation current shown in FIG. 14, the oxidation current, which should decreases monotonically in normal circumstances, suddenly increases instantaneously, as circled in the figure. When such a phenomenon happens to occur at the time point for measuring the oxidation current for computing the blood glucose level, the computation result becomes higher than the actual blood glucose level.

The inventors of the present invention checked a plurality of samples in which the above-described phenomenon was seen. As a result, it was found that, as a feature common to these samples, blood BL had reached beyond the edge 97a of the air vent 97 on the surface of the substrate 92, as shown in FIG. 15. On the other hand, in the samples in which the sudden increase of the oxidation current did not occur, blood BL was stopped at the edge 97a of the air vent 97 (See FIG. 13).

Conceivably, from the above difference, the sudden increase of oxidation current is caused by the remove of the blood BL, i.e., the phenomenon that the blood BL once stopped at the edge 97a of the air vent 97 moves beyond the edge 97a of the air vent 97.

Specifically, when voltage is applied to the liquid phase reaction system including the blood BL, electrons are transferred between the electron mediator and the end 90a of the working electrode 90. Therefore, in the state in which the movement of the blood BL is suspended, the proportion of reductant is low at the surface of the end 90a of the working electrode 90, so that the oxidation current decreases. In this state, when the blood BL moves, reductant moves from the introduction port 96 side to the surface of the end 90a of the working electrode 90, so that the proportion of the reductant at the surface of the end 90a temporarily increases. As a result, the amount of electrons transferred between the reductant and the surface of the end 90a of the working electrode 90 suddenly increases, so that the oxidation current does not monotonically decrease but increases temporarily.

DISCLOSURE OF THE INVENTION

An object of the present invention is to prevent, in performing analysis of a sample by using an analytical tool, the sample liquid loaded into a capillary formed on the substrate of the analytical tool from moving further so that the sample can be analyzed properly.

According to the present invention, there is provided an analytical tool comprising a substrate, a capillary which is formed on the substrate and into which a sample liquid is to be loaded by movement of the sample liquid in the capillary. The substrate is provided with a liquid movement preventer for preventing the sample liquid loaded into the capillary from moving further.

For example, the liquid movement preventer includes a stepped portion projecting from the substrate. For example, the stepped portion comprises a conductive layer formed on the substrate and an insulating layer covering the conductive layer.

For example, the analytical tool further comprises a plurality of electrodes provided on the substrate for applying voltage to the sample liquid.

For example, the conductive layer is formed as a dummy electrode which does not contribute to the voltage application to the sample liquid. The dummy electrode is formed simultaneously with the plurality of electrodes.

For example, the plurality of electrodes include a detection electrode for detecting whether or not the sample liquid of an amount necessary for analysis is supplied into the capillary. In this case, the conductive layer may be provided by the detection electrode. Alternatively, the conductive layer may be provided by an electrode other than the detection electrode.

The analytical tool may further comprise an air vent for discharging air from the capillary in moving the sample liquid in the capillary. In this case, the insulating layer includes an opening which exposes part of the electrodes and which extends along the capillary. Preferably, as viewed in a thickness direction of the substrate, the most downstream point of the opening in a flow direction of the sample liquid is located on the same line or almost same line as the most upstream point of the air vent in the flow direction of the sample liquid.

The liquid movement preventer may include a recess provided at the substrate.

For example, the recess comprises a through-hole penetrating through the substrate. Preferably, when the analytical tool includes an air vent, the air vent is arranged coaxially or generally coaxially with the through-hole in the thickness direction of the substrate.

Preferably, as viewed in the thickness direction of the substrate, the most upstream point of the recess in a flow direction of the sample liquid is located on a same line or almost same line as the most upstream point of the air vent in the flow direction of the sample liquid.

BEST MODE FOR CARRYING OUT THE INVENTION

Biosensors according to a first through a fifth embodiments of the present invention will be described below.

First, referring to FIGS. 1 through 4, a biosensor according to the first embodiment of the present invention will be described.

Figure 1:
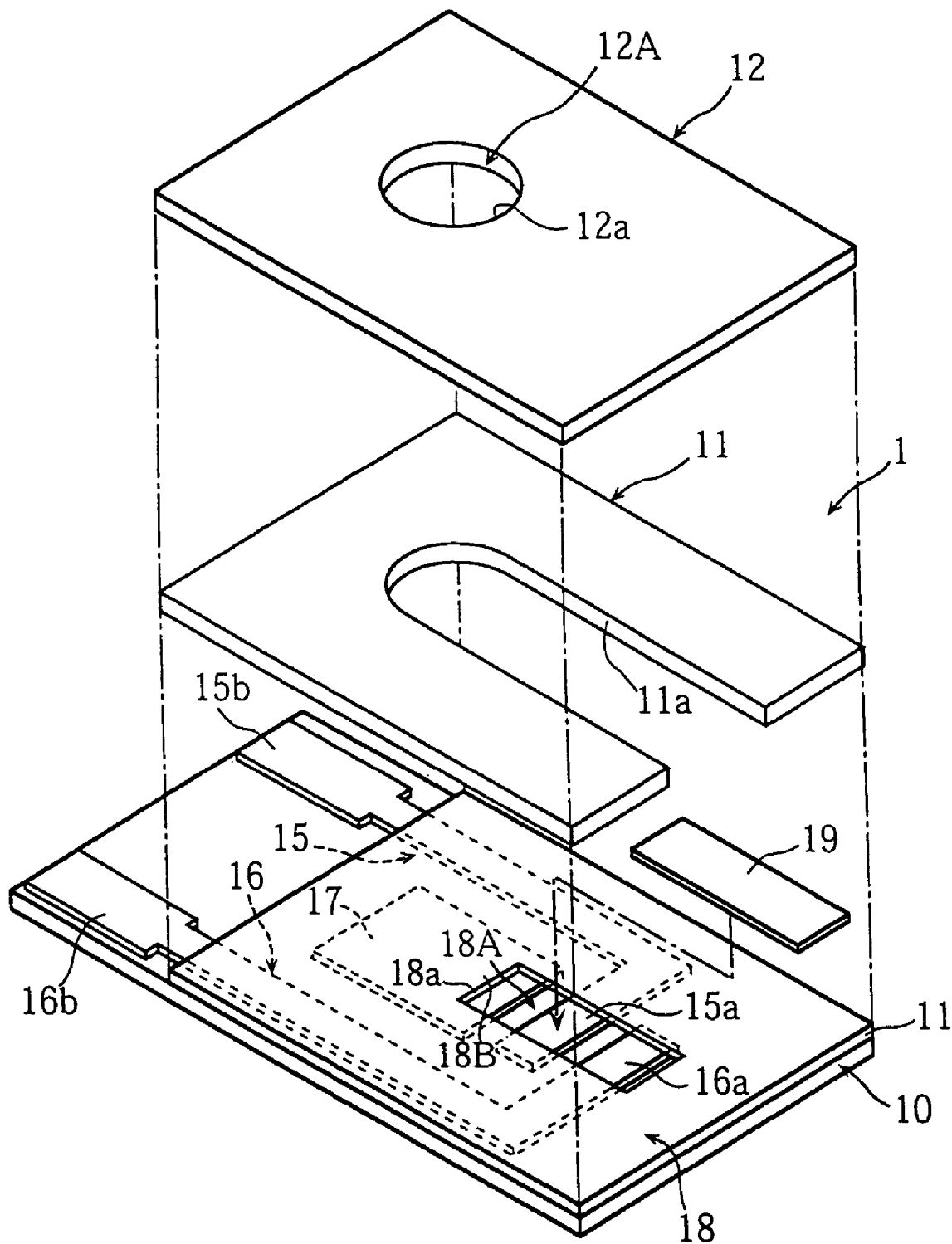
FIG. 1 is an exploded perspective view of a biosensor according to a first embodiment of the present invention.
Figure 2:
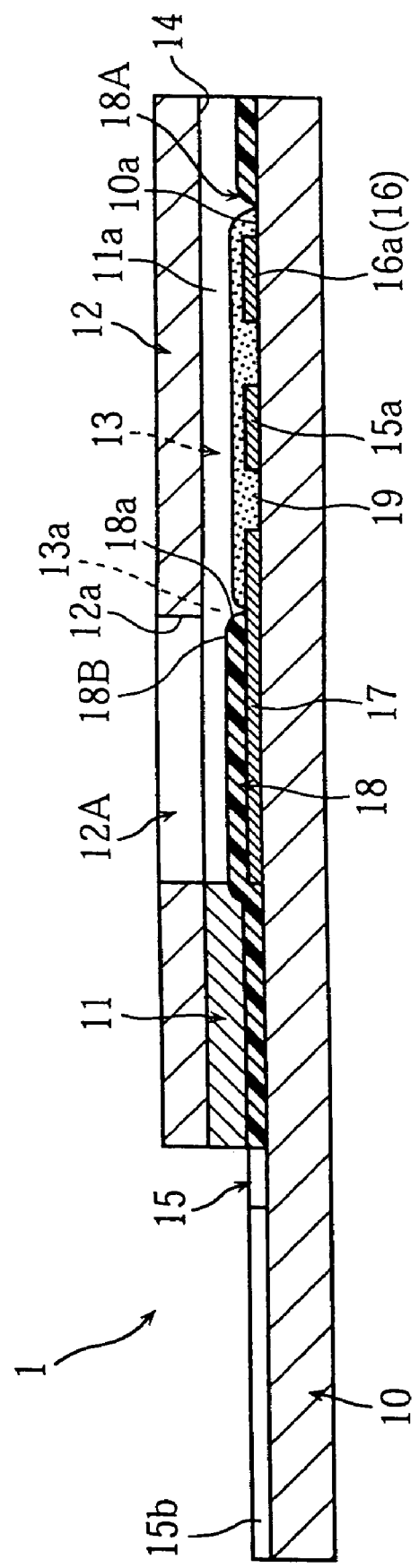
FIG. 2 is a sectional view of the biosensor shown in FIG. 1.
Figure 3:
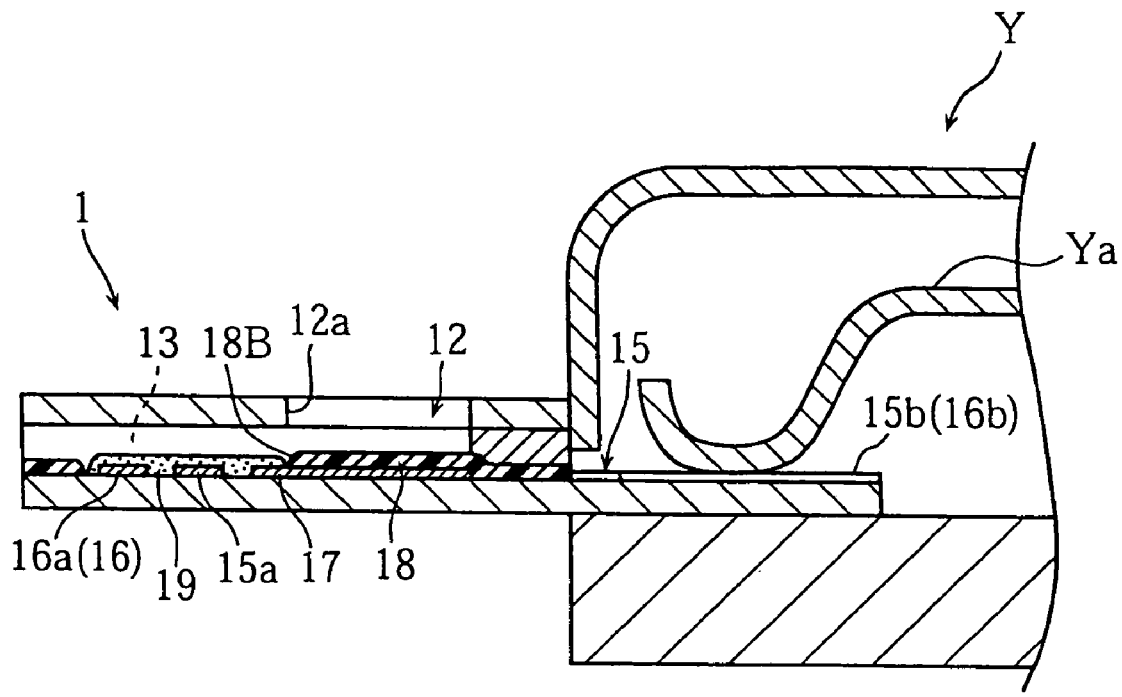
FIG. 3 is a sectional view for describing a method for measuring a blood glucose level by using the biosensor shown in FIG. 1.
Figure 4:
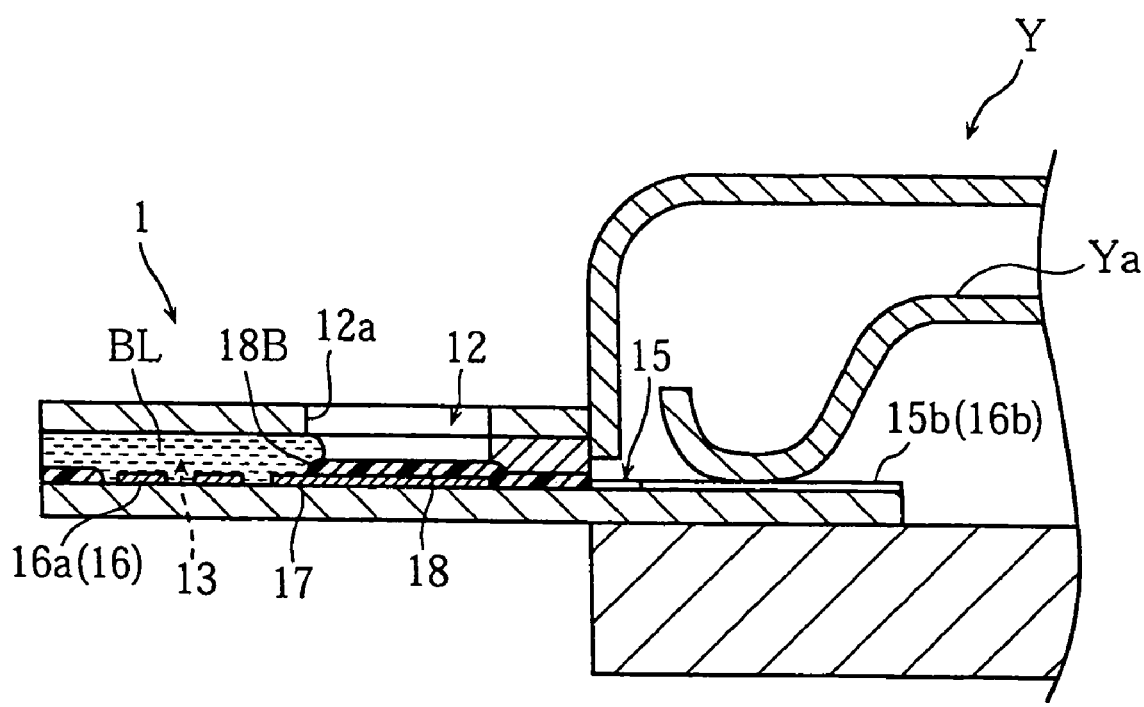
FIG. 4 is a sectional view for describing a method for measuring a blood glucose level by using the biosensor shown in FIG. 1.

The biosensor 1 shown in FIGS. 1 and 2 is a disposable one and mounted, in use, to a concentration measuring apparatus Y, as shown in FIGS. 3 and 4.

As shown in FIGS. 1 and 2, the biosensor 1 includes an elongated rectangular substrate 10, and a cover 12 stacked on the substrate via a spacer 11. In the biosensor 1, the components 10-12 define a capillary 13 extending longitudinally of the substrate 10. The capillary 13 is utilized for moving the blood introduced through an introduction port 14 in the longitudinal direction of the substrate 10 by capillary action and for retaining the introduced blood.

The spacer 11 serves to define the height of the capillary 13. The spacer 11 is formed with a slit 11a having an open front end. The slit 11a defines the width of the capillary 13. The open front end of the slit 11a constitutes the introduction port 14 for introducing blood into the capillary 13.

The cover 12 is formed with a through-hole 12A. The through-hole 12A serves to discharge air in the capillary 13 to the outside. The cover may be made of a vinylon, for example, to be entirely hydrophilic. Alternatively, the surface of the cover which faces the capillary 13 may be hydrophilically treated. The hydrophilization may be performed by the ultraviolet radiation or by the application of a surface-active agent such as lecithin.

The substrate 10 has an upper surface 10a formed with a working electrode 15, a counter electrode 16, a dummy electrode 17, an insulating film 18 and a regent portion 19.

The working electrode 15 and the counter electrode 16 are utilized for applying a voltage to the blood in the capillary 13 or for measuring the amount of electrons supplied from the blood as a responsive current. The working electrode 15 and the counter electrode 16 have respective first ends 15a and 16a for coming into contact with the blood. The first ends 15a and 16a extend widthwise of the substrate 10 and are spaced from each other longitudinally of the substrate. The working electrode 15 and the counter electrode 16 have respective second ends 15b and 16b for coming into contact with terminals Ya (See FIGS. 3 and 4) provided in the concentration measuring apparatus Y. The working electrode 15 and the counter electrode 16 can be formed by screen printing using conductive paste. Specifically, use may be made of conductive paste containing carbon powder, binder resin and a solvent.

The dummy electrode 17 serves to raise the height of the insulating film 18 at the most upstream point 12a of the through-hole 12A of the cover 12. The dummy electrode is aligned with the ends 15a, 16a of the working electrode 15 and the counter electrode 16 in the longitudinal direction of the substrate 10.

The dummy electrode 17 can be formed simultaneously with the working electrode 15 and the counter electrode 16 by screen printing, for example. Therefore, the manufacture of the biosensor 1 does not require the additional step for forming the dummy electrode 17, so that a deterioration of the operation efficiency can be prevented.

The insulating film 18 covers most portions of the working electrode 15, the counter electrode 16 and the dummy electrode 17. The insulating film 18 includes an opening 18A located in the capillary 13. Through the opening 18A, part of the ends 15a, 16a of the working electrode 15 and the counter electrode 16 and part of the dummy electrode 17 are exposed. The opening 18A has a downstream edge 18a located almost directly below the most upstream point 12a of the through-hole 12A. Therefore, at the downstream edge 13a of the capillary 13, the dummy electrode 17 and part of the insulating film 18 project upward from the upper surface 10a of the substrate 10 to form a stepped portion 18B. As a result, the sectional area of the capillary at the downstream edge 13a is made smaller than other portions. Therefore, at the downstream edge 13a of the capillary 13, blood existing on the upper surface 10a of the substrate 10 is prevented from moving.

The reagent portion 19, which may be in e.g. a solid state, is arranged to bridge the end 15a of the working electrode 15 and the end 16a of the counter electrode 16 while closing the opening 18A of the insulating film 18. The reagent portion 19 contains a relatively large amount of electron mediator, and a relatively small amount of oxidoreductase dispersed in the electron mediator. As the electron mediator, use may be made of a complex of iron or Ru, for example. Examples of usable iron complex include potassium ferricyanide, whereas examples of usable Ru complex include one that includes $NH_3$ as a ligand. The oxidoreductase is selectable depending on the kind of a particular component contained in a sample liquid as the measurement target. For example, the particular component may be glucose or cholesterol. Examples of oxidoreductase for such particular components include glucose dehydrogenase, glucose oxidase, hexokinase, cholesterol dehydrogenase and cholesterol oxidase.

As shown in FIG. 3, the biosensor 1 is mounted, in use, to a concentration measuring apparatus Y which includes a pair of terminals Ya. Though not illustrated in the figure, in addition to the paired terminals, the apparatus includes an analytical circuit for analyzing the blood introduced to the biosensor 1. The terminals Ya are so arranged as to come into contact with the ends 15b, 16b of the working electrode 15 and the counter electrode 16 when the biosensor 1 is mounted to the concentration measuring apparatus Y. For example, the analytical circuit has the function of applying a voltage through the paired terminal Ya to measure the responsive current and the function to perform computation necessary for the analysis of the blood based on the responsive current.

As shown in FIGS. 3 and 4, when blood BL is introduced into the capillary 13 with the biosensor 1 mounted to the concentration measuring apparatus Y, the blood BL moves through the capillary 13 by capillary action and then stops at the most upstream point 12a of the through-hole 12A of the cover 12.

In the capillary 13, the reagent portion 19 is dissolved by the introduction of the blood BL, and a liquid phase reaction system is established by the electron mediator, the oxidoreductase and the blood, for example. At this time, for example, the particular component contained in the blood BL is oxidized, while the electron mediator is reduced. As a result, in the liquid phase reaction system, the reduced product of the electron mediator is generated in accordance with the concentration of the particular component in the blood BL. When a voltage is applied to the liquid phase reaction system through the working electrode 15 and the counter electrode 16, electrons are transferred between the reduced product of the electron mediator and the end 15a of the working electrode 15, for example. In the concentration measuring apparatus Y, the analytical circuit measures the amount of the transferred electrons as e.g. the oxidation current, and the concentration of the particular component in the blood BL is computed based on the measurement result. The computation of the concentration is performed by applying the measured current to a calibration curve prepared in advance for indicating the relationship between current and concentration.

In the biosensor 1, the stepped portion 18B provided by the dummy electrode 17 and the insulating film 18 prevents the blood BL loaded into the capillary 13 from moving further. Therefore, in the biosensor 1, a sudden increase in the current, which is generated by the electron transfer between the electron mediator and the working electrode 15, is prevented. Therefore, in the biosensor 1, a deterioration of the analysis accuracy due to the remove of the blood can be prevented.

In the biosensor 1, the bottom of the insulating film 18 is raised by the dummy electrode 17 at a portion corresponding to the most upstream point 12a of the through-hole 12A of the cover 12. However, the bottom of the insulating film 18 at that portion may be raised by the working electrode 15 or the counter electrode 16 by changing the position of the working electrode 15 or the counter electrode 16.

Next, biosensors according to the second through the fifth embodiments of the present invention will be described with reference to FIGS. 5 through 10. In the figures referred to hereinafter, the elements which are identical or similar to those of the foregoing biosensor 1 are indicated by the same reference signs, and the description thereof will be omitted.

Figure 5:
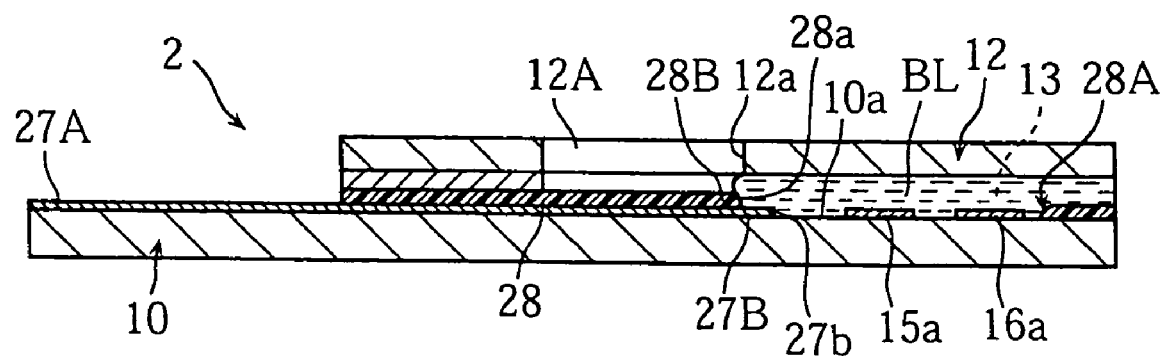
FIG. 5 is a sectional view of a biosensor according to a second embodiment of the present invention.
Figure 6:
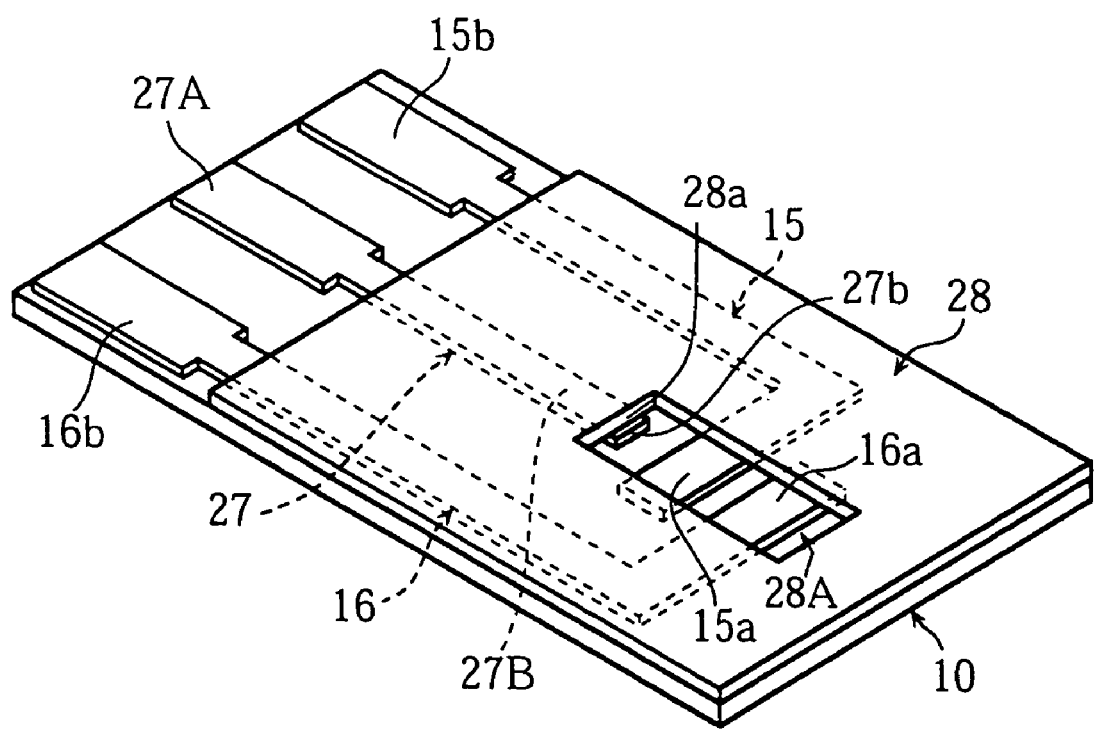
FIG. 6 is a perspective view of the biosensor shown in FIG. 5, from which the cover and the spacer are removed.

FIGS. 5 and 6 show a biosensor 2 according to the second embodiment of the present invention and the principal portion thereof.

The biosensor 2 includes a detection electrode 27 in addition to a working electrode 15 and a counter electrode 16. Instead, the dummy electrode 17 (See FIGS. 1 and 2) is omitted.

The detection electrode 27, in combination with the working electrode 15 and the counter electrode 16, serves to detect whether or not blood BL of the amount necessary for the analysis is loaded into the capillary 13. The detection electrode 27 is covered by the insulating film 28 except an end 27A. The detection electrode 27 has another end 27B whose upstream edge 27b is positioned slightly upstream of the most upstream point 12a of the through-hole 12A of the cover 12.

The insulating film 28 is formed with an opening 28A. The opening 28A exposes the ends 15a and 16a of the working electrode 15 and the counter electrode 16. The opening 28A includes a downstream edge 28a positioned directly below the most upstream point 12a of the through-hole 12A of the cover 12.

In the biosensor 2, the downstream edge 28a of the opening 28A is raised by the end 27B of the detection electrode 27, whereby a stepped portion 28B is formed on the substrate 10 at a portion corresponding to the most upstream point 12a of the through-hole 12A. Therefore, also in the biosensor 2, the blood BL is prevented from moving further along the upper surface 10a of the substrate 10, so that the analysis of the blood BL can be properly performed.

The biosensor may include a pair of detection electrodes, and whether or not blood BL of the amount necessary for the analysis is loaded into the capillary may be detected by the paired detection electrodes. In such a case, a stepped portion for preventing the blood from moving further may be provided by one of the paired detection electrodes.

Figure 7:
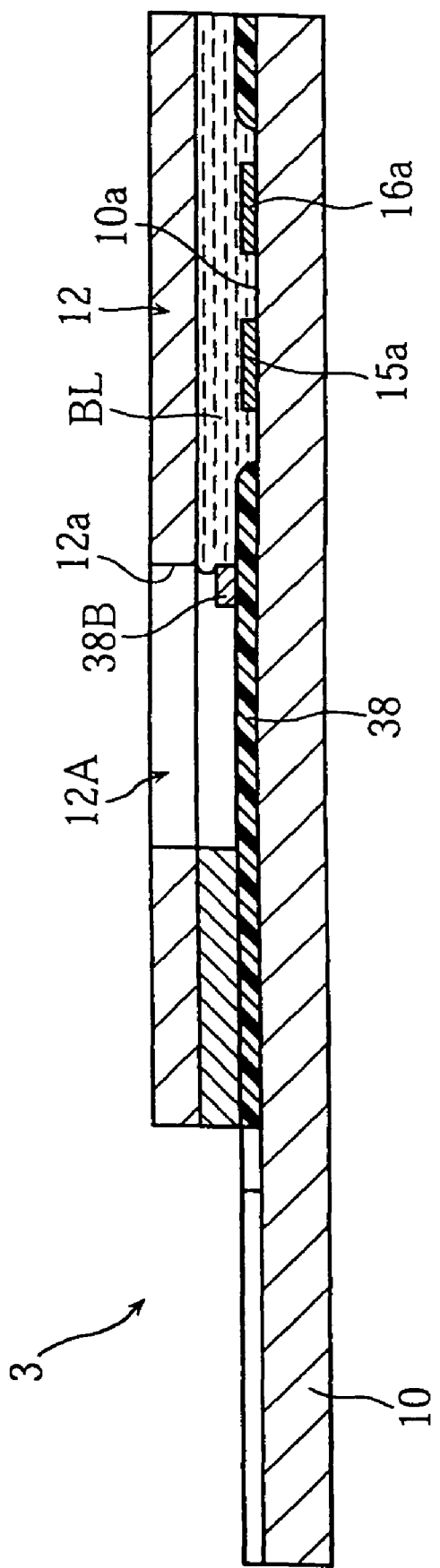
FIG. 7 is a sectional view of a biosensor according to a third embodiment of the present invention.

FIG. 7 shows a biosensor 3 according to the third embodiment of the present invention. The biosensor 3 includes an insulating layer 38 formed with a projection 38B. The projection 38B is provided at a portion corresponding to the most upstream point 12a of the through-hole 12A of the cover 12.

In the biosensor 3, the projection 38B prevents the blood BL from moving further along the upper surface 10a of the substrate 10, so that the analysis of the blood BL can be performed properly.

The projection 38B may be provided by either of a conductive member and an insulating member. The projection 38B may be formed directly on the upper surface 10a of the substrate 10.

Figure 8:
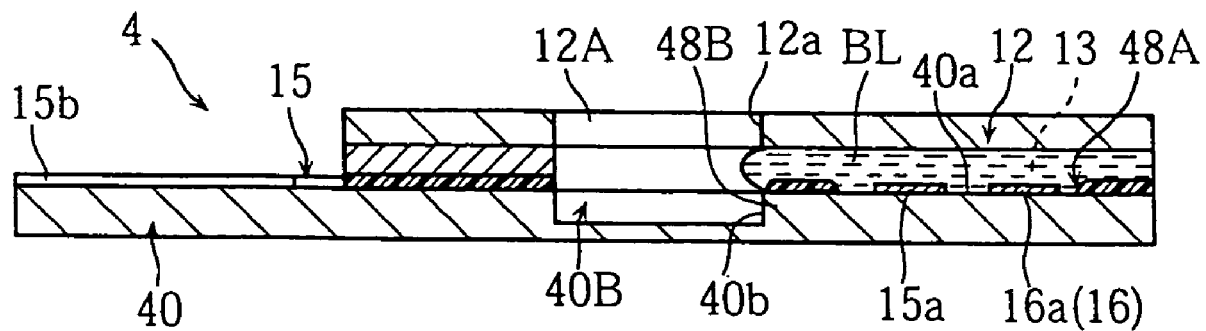
FIG. 8 is a sectional view of a biosensor according to a fourth embodiment of the present invention.
Figure 9:
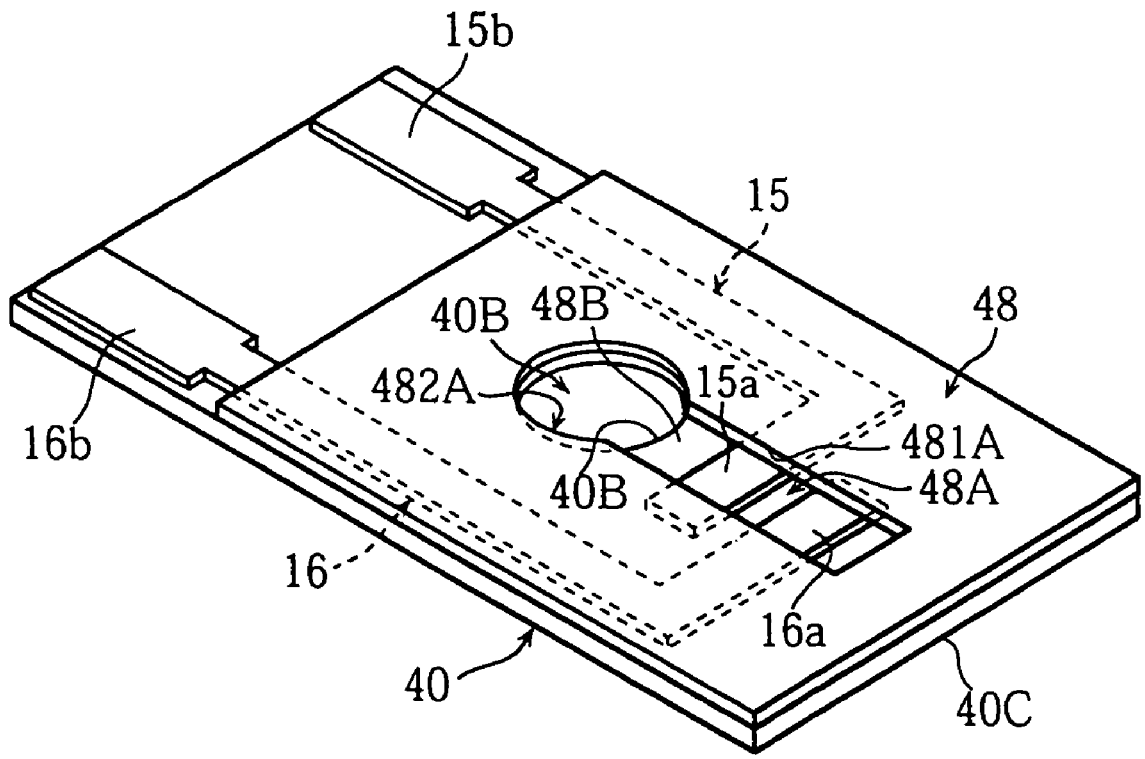
FIG. 9 is a perspective view of the biosensor shown in FIG. 8, from which the cover and the spacer are removed.

FIGS. 8 and 9 show a biosensor 4 according to the fourth embodiment of the present invention and the principal portion thereof.

The biosensor 4 includes a substrate 40 formed with a recess 40B. The recess 40B is circular and has a most upstream point 40b positioned directly below the most upstream point 12a of the through-hole 12A of the cover 12.

Similarly to the first embodiment, the working electrode 15 and the counter electrode 16 are covered by an insulating film 48 formed with an opening 48A. The opening 48A of the insulating film 48 includes a linear opening portion 481A and a circular opening portion 482A. The linear opening portion 481A extends from adjacent an end edge 40C of the substrate 40 to a most upstream point 40b of the recess 40B. The circular opening portion 482A is connected to the linear opening portion 481A and has a circular shape for exposing the recess 40B.

In the biosensor 4, the recess 40B provides a stepped portion 48B directly below the most upstream point 12a of the through-hole 12A of the cover 12. In the biosensor 4, therefore, the stepped portion 48B (recess 40B) prevents the blood BL from moving further along the upper surface 40b of the substrate 40, so that the analysis of the blood BL can be performed properly.

The configuration of the recess 40B is not limited to circular. For example, the recess may have another configuration such as polygonal.

Figure 10:
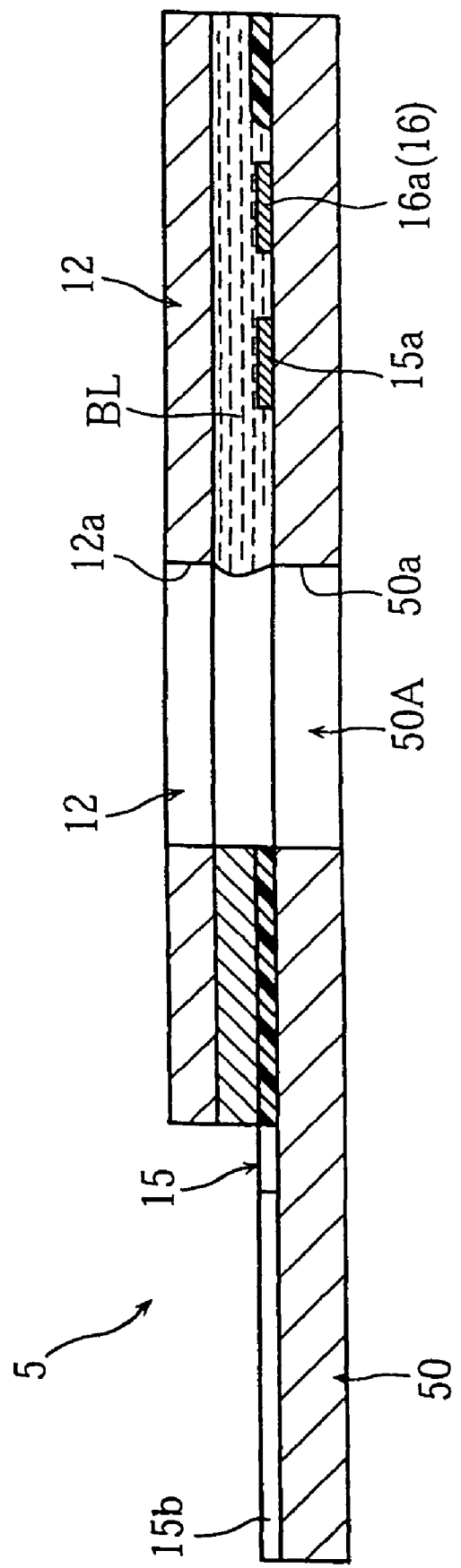
FIG. 10 is a sectional view of a biosensor according to a fifth embodiment of the present invention.
Figure 11:
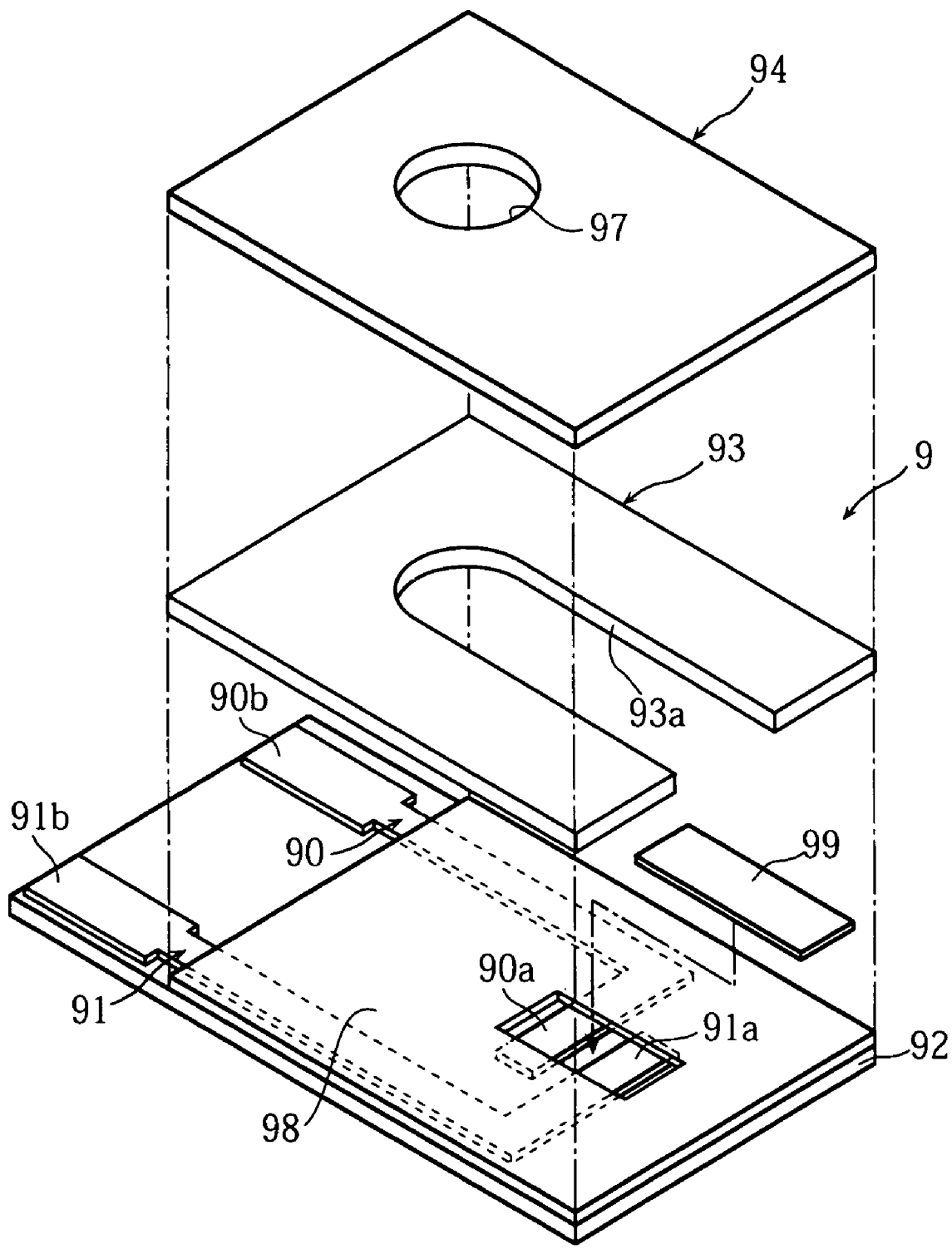
FIG. 11 is an exploded perspective view showing an example of prior art biosensor.
Figure 12:
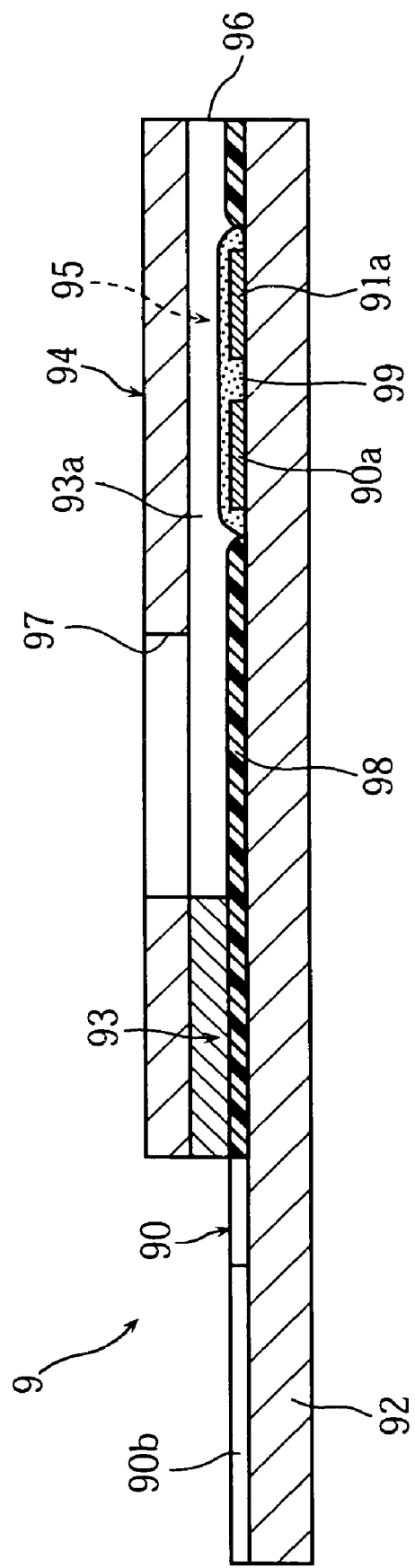
FIG. 12 is a sectional view of the biosensor shown in FIG. 11.
Figure 13:
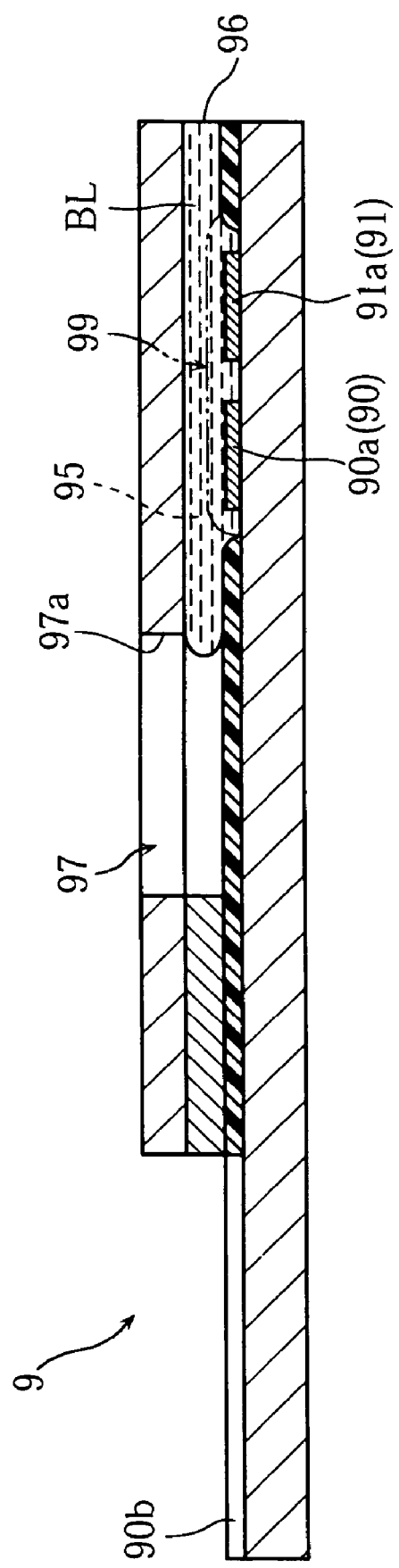
FIG. 13 is a sectional view showing the biosensor of FIG. 11 in a state in which blood is introduced into the capillary.
Figure 14:
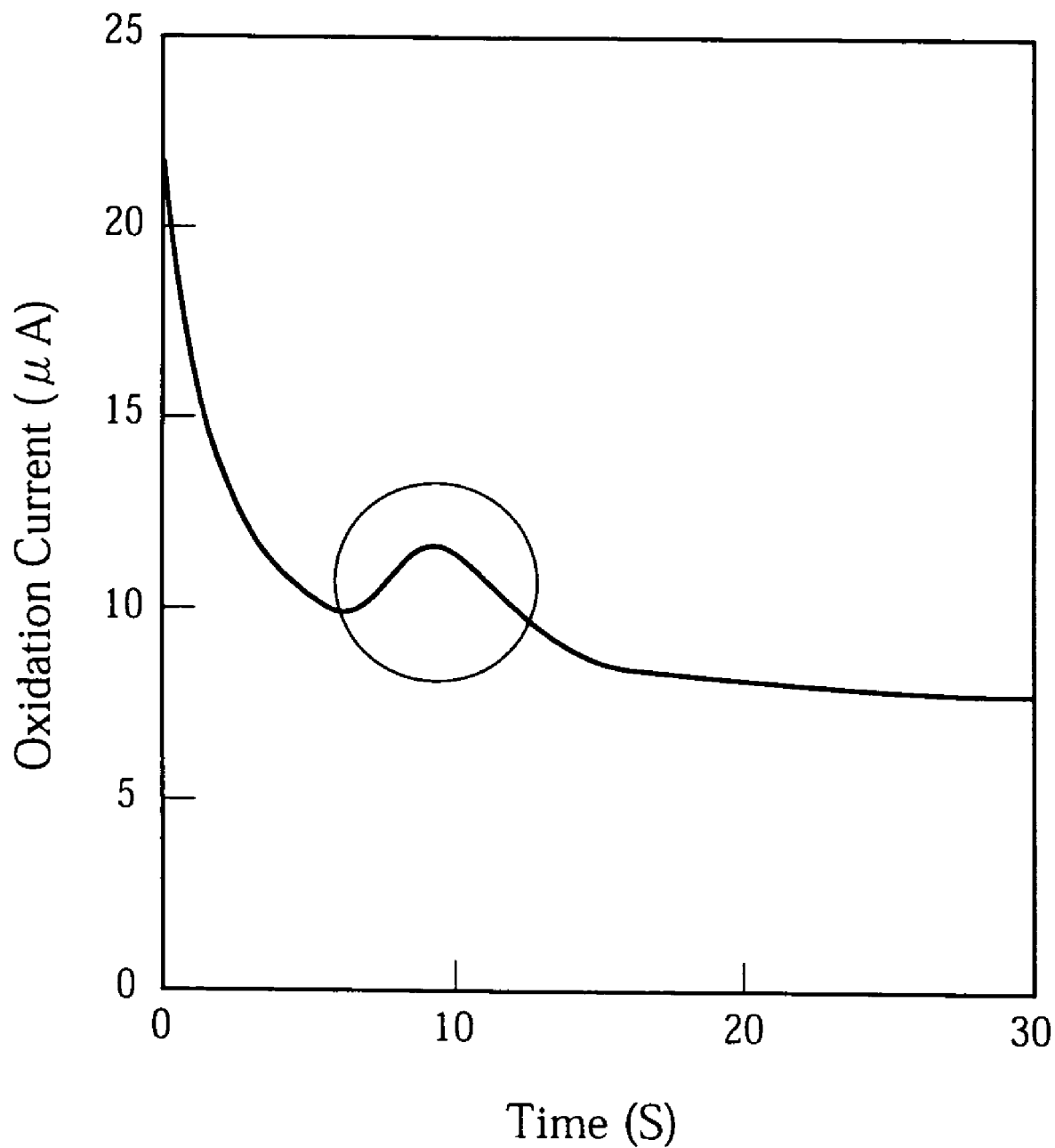
FIG. 14 is a graph showing an example of time course in which the responsive current suddenly increases when the biosensor shown in FIG. 11 is used.
Figure 15:
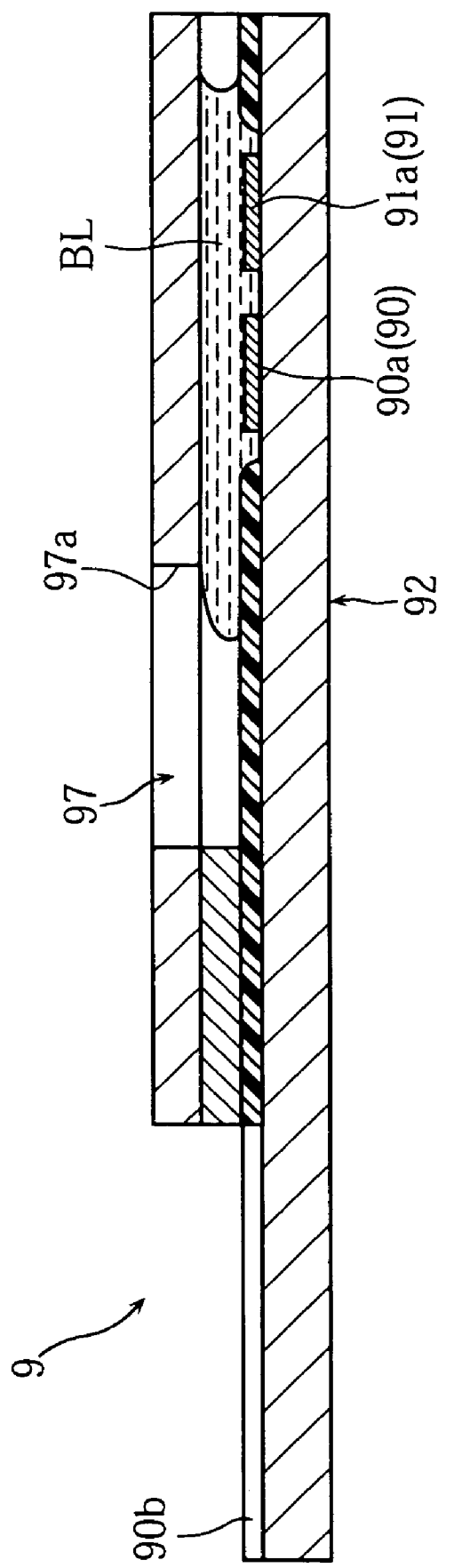
FIG. 15 is a sectional view showing the biosensor of FIG. 11 in a state in which the blood has moved after the introduction into the capillary.

FIG. 10 shows a biosensor 5 according to the fifth embodiment of the present invention.

In the biosensor 5, instead of the recess 40A (See FIGS. 8 and 9) of the biosensor 4 of the fourth embodiment, a through-hole 50A is formed in the substrate 50. The through-hole 50A is provided directly below the through-hole 12A of the cover 12 and has a configuration corresponding to the trough-hole 12A. Thus, the most upstream point 50a of the through-hole 12A of the substrate 50 is located directly below the most upstream point 12a of the through-hole 12A of the cover 12. The through-hole 50A of the substrate 50 can be formed simultaneously with the through-hole 12A of the cover 12 by punching.

In the biosensor 5 again, by the operation similar to that of the biosensor 4 (See FIGS. 8 and 9), the through-hole 50A prevents the blood BL from moving further, so that the analysis of the blood BL can be performed properly.

In the biosensor 5, the through-hole 50A of the substrate 50 can be utilized for discharging air from the capillary 13. In such a case, the through-hole 12A of the cover 12 can be dispensed with.

The through-hole 50A of the substrate 50 is not limited to circular one but may have another configuration.

Although the above-described biosensors 1-5 are designed for analyzing a particular component in blood, the present invention is applicable to the analysis of a particular component in a sample liquid other than blood, such as urine, saliva or industrial wastewater.

The present invention is not limited to a biosensor for analyzing a sample liquid by the electrode method and is applicable to a biosensor for analyzing a sample liquid by colorimetry.

The invention claimed is:

1. An analytical tool comprising:
   a substrate;
   a cover stacked on the substrate via a spacer;
   a capillary formed between the substrate and the cover, the capillary including an introduction port for taking a sample liquid into the capillary;
   a stepped portion projecting from the substrate for preventing the sample liquid in the capillary from moving further; and
   a reagent portion provided in the capillary between the introduction port and the stepped portion;
   wherein the stepped portion is greater in height with respect to the substrate than the reagent portion,
   wherein the cover is formed with an air vent hole for discharging air from the capillary when the sample liquid moves in the capillary,
   wherein the stepped portion is located at a position corresponding to an edge portion of the air vent hole for preventing the sample liquid in the capillary from moving beyond the edge portion to flow out through the air vent hole.

2. The analytical tool according to claim 1, wherein the stepped portion comprises a conductive layer formed on the substrate and an insulating layer covering the conductive layer.

3. The analytical tool according to claim 2, further comprising a plurality of electrodes provided on the substrate for applying voltage to the sample liquid.

4. The analytical tool according to claim 3, wherein the conductive layer is formed as a dummy electrode which does not contribute to the voltage application to the sample liquid.

5. The analytical tool according to claim 4, wherein the dummy electrode is formed simultaneously with the plurality of electrodes.

6. The analytical tool according to claim 3, wherein the plurality of electrodes include a detection electrode for detecting whether or not the sample liquid of an amount necessary for analysis is supplied into the capillary, and
   wherein the conductive layer is provided by the detection electrode.

7. The analytical tool according to claim 3,
   wherein the insulating layer includes an opening which exposes part of the electrodes and which extends along the capillary; and
   wherein, as viewed in a thickness direction of the substrate, a most downstream point of the opening in a flow direction of the sample liquid is located on a same line or almost same line as a most upstream point of the air vent hole in the flow direction of the sample liquid.

* * * * *